(12) United States Patent
Rigler et al.

(10) Patent No.: US 11,609,184 B2
(45) Date of Patent: Mar. 21, 2023

(54) APPARATUS FOR CHARACTERIZING LUMINESCENT ENTITIES

(71) Applicant: Gnothis AB, Trosa (SE)

(72) Inventors: Rudolf Rigler, Djursholm (SE); Lars Edman, Stockholm (SE); Daniel Rönnlund, Solna (SE); Margo Tiiman, Solna (SE)

(73) Assignee: Gnothis AB, Trosa (SE)

( * ) Notice: Subject to any disclaimer, the term of this patent is extended or adjusted under 35 U.S.C. 154(b) by 0 days.

(21) Appl. No.: 16/466,372

(22) PCT Filed: Dec. 5, 2017

(86) PCT No.: PCT/EP2017/081526
§ 371 (c)(1),
(2) Date: Jun. 4, 2019

(87) PCT Pub. No.: WO2018/104301
PCT Pub. Date: Jun. 14, 2018

(65) Prior Publication Data
US 2019/0293562 A1    Sep. 26, 2019

(30) Foreign Application Priority Data

Dec. 5, 2016 (EP) .................................. 16202282

(51) Int. Cl.
*G01N 21/64* (2006.01)
*C12Q 1/6874* (2018.01)
(Continued)

(52) U.S. Cl.
CPC ......... *G01N 21/648* (2013.01); *C12Q 1/6874* (2013.01); *G01N 21/6456* (2013.01);
(Continued)

(58) Field of Classification Search
CPC ............. G01N 21/648; G01N 21/6456; G01N 21/6458; G01N 21/6408; G01N 21/6445;
(Continued)

(56) References Cited

U.S. PATENT DOCUMENTS

| 7,196,787 B2 * | 3/2007 | Uhl | G01N 21/552 |
| | | | 356/317 |
| 2004/0023229 A1 * | 2/2004 | Rigler | G01N 21/6428 |
| | | | 435/6.12 |

(Continued)

FOREIGN PATENT DOCUMENTS

WO   2012/177206 A1   12/2012

OTHER PUBLICATIONS

Ming Lei et al: "Total-internal-reflection fluorescence microscopy with W-shaped axicon mirrors", Optics Letters, vol. 35, No. 23, Dec. 1, 2010, p. 4057-4059.

(Continued)

*Primary Examiner* — David P Porta
*Assistant Examiner* — Djura Malevic
(74) *Attorney, Agent, or Firm* — Rothwell, Figg, Ernst & Manbeck, P.C.

(57) ABSTRACT

An apparatus for characterizing luminescent entities by excitation comprising: • a substrate (6) being in contact with a solution comprising luminescent entities; • a source of electromagnetic radiation (4) providing at least a primary beam of radiation (8); an objective (5); a first optical element (1) capable of transforming the intensity profile of the primary beam (8) into an arbitrary secondary intensity profile (distribution) (9); a second optical element (2) capable of separating (discriminating) radiation by wavelength; and a detector (7), where the arbitrary secondary intensity profile has at least an off-center circular continuous intensity distribution (33) focused on the back focal plane (Continued)

(12) of the objective forming a collimated beam (10) capable of creating an evanescent field on the side of the substrate where the solution comprising luminescent entities are located, where the evanescent field excites the luminescent entities thereby creating emission radiation separated by the second optical element (2) and captioned by the detector (7). The invention also relates to an apparatus comprising two optical elements providing a final third intensity profile (distribution) which is the convolution of two mathematical transformations corresponding to each of optical element one and four, respectively.

24 Claims, 8 Drawing Sheets

(51) Int. Cl.
G02B 27/56 (2006.01)
G02B 21/00 (2006.01)
G02B 21/16 (2006.01)

(52) U.S. Cl.
CPC ....... *G01N 21/6458* (2013.01); *G02B 21/004* (2013.01); *G02B 21/0076* (2013.01); *G02B 21/16* (2013.01); *G02B 27/56* (2013.01); *G01N 21/6408* (2013.01); *G01N 21/6445* (2013.01); *G01N 21/6452* (2013.01); *G01N 2021/6419* (2013.01); *G01N 2021/6463* (2013.01); *G01N 2021/6478* (2013.01)

(58) Field of Classification Search
CPC ....... G01N 21/6452; G01N 2021/6419; G01N 2021/6463; G01N 2021/6478; C12Q 1/6874; G02B 21/004; G02B 21/0076; G02B 21/16; G02B 27/56
See application file for complete search history.

(56) References Cited

U.S. PATENT DOCUMENTS

| 2006/0126063 | A1* | 6/2006 | Cluzel | G01N 21/6458 356/318 |
|---|---|---|---|---|
| 2010/0315708 | A1 | 12/2010 | Amberger | |
| 2011/0278475 | A1* | 11/2011 | Lundquist | G01N 27/44721 250/459.1 |
| 2016/0326581 | A1* | 11/2016 | Rigler | C12Q 1/6874 |

OTHER PUBLICATIONS

M. Beck et al: "Sub-100-nanometre resolution in total internal reflection fluorescence microscopy", Journal of Microscopy, vol. 232, No. 1, Sep. 25, 2008, pp. 99-105.
International Search Report and Written Opinion cited in PCT/EP2017/081526 dated Mar. 8, 2018, 16 pages.

* cited by examiner

APPARATUS FOR CHARACTERIZING LUMINESCENT ENTITIES

BACKGROUND

The present invention relates to an apparatus which can be used for a variety of applications specifically in the biomedical field. Relevant applications relate to the sequencing of nucleic acids and imaging. One of the fundamental aspects of the invention is the application of optical elements which are capable of transforming an incident beam of electromagnetic radiation into an arbitrary secondary intensity profile (distribution) which intensity profile has at least an off-center circular continuous intensity distribution and is focused on the back focal plane of an objective. At least a part of the secondary discrete intensity profile is focused on areas of the back focal plane of an objective such that the transmitted radiation leaves the objective at an angle which is total internally reflected on a substrate. The total internally reflected radiation creates an evanescent field on one side of the substrate. The evanescent field is used for excitation of luminescent entities comprised in a solution in contact with the substrate. The emitted radiation is captured by a detector, said emitted radiation being separated from the excitation radiation by suitable optical elements. The emitted radiation is used for evaluation/characterization/analyzation of static as well as temporal phenomena occurring within the evanescent field.

The invention also encompasses an apparatus incorporating two optical elements capable of transforming the intensity distribution of electromagnetic radiation, where the two optical elements are diffractive optical elements and the intensity profile 'down stream' the second optical element is the convolution of two mathematical transformations corresponding to each of optical elements, respectively Optical elements splitting an incident beam of light into a plurality of light beams have been used in methods for excitation of molecules. US 2008/0277595 A1 and U.S. Pat. No. 7,259,847 B2 disclose methods using optical elements which multiplies an incident light beam. The transmitted multiple light beams are transmitted through an objective and ultimately focused at a location within the solution comprising the entities of analysis. Hence, the methods disclosed in the two documents relate to methods creating a multitude of confocally illuminated volumes within the solutions comprising the compounds to be analyzed. Neither of the two US documents disclose methods accommodating to focus the transmitted multiple light beams of light on the pack-focal plane of an objective.

One advantage of the present invention is that the loss of photons is reduced. Moreover, by the provision of an intensity profile having an off-center circular continuous intensity distribution focused on the back focal plane of an objective, collimated beams are formed creating overlapping evanescent fields. By the creation of an evanescent field from focusing an off-center circular continuous intensity distribution possible defects and diffraction patterns of individual fields are effectively suppressed since it is the convolution of all fields that forms the final evanescent field area. Also, the shape of the final evanescent field area becomes the convolution of all shapes which gives the possibility to control the shape of the area by selection of how the primary beam is split into secondary beams by the use of an optical element. By focusing an off-center circular continuous intensity distribution to the back focal plane the resulting 'convoluted' field will be much more uniform than the individual fields from discrete intensity distributions.

BRIEF SUMMARY OF THE INVENTION

The invention relates to an apparatus for characterizing luminescent entities by excitation comprising: a substrate (5) being in contact with a solution comprising luminescent entities; a source of electromagnetic radiation (4) providing at least a primary beam of radiation (8); an objective (5); a first optical element (1) capable of transforming the intensity profile of the primary beam into an arbitrary secondary intensity profile (distribution); a second optical element (2) capable of separating (discriminating) radiation by wavelength; and a detector (7); where the arbitrary secondary intensity profile having at least an off-center circular continuous intensity distribution is focused on the back focal plane (x) of the objective such that at least a collimated beam is obtained capable of creating an evanescent filed on the side of the substrate where the solution comprising luminescent entities are located, wherein the evanescent field excites the luminescent entities thereby creating emission radiation separated by the first optical element (2) and captioned by the detector (7).

Furthermore, the invention also embraces an apparatus for characterizing luminescent entities by excitation comprising: a substrate being in contact with a solution comprising luminescent entities; a source of electromagnetic radiation providing at least a primary beam of radiation; an objective; a first optical element capable of transforming the intensity profile of the primary beam into an arbitrary secondary intensity profile (distribution); a second optical element capable of separating (discriminating) radiation by wavelength; a fourth optical element capable of transforming the secondary discrete intensity profile (distribution) into an arbitrary third intensity profile (distribution); and a detector; where first and forth optical elements are diffractive optical elements, where the arbitrary third intensity profile is focused on the back focal plane of the objective such that at least a collimated beam is obtained capable of creating an evanescent field on the side of the substrate where the solution comprising luminescent entities are located, where the evanescent field excites the luminescent entities thereby creating emission radiation separated by the first optical element and captioned by the detector, and wherein and the third intensity profile (distribution) is the convolution of two mathematical transformations corresponding to each of optical element one and four, respectively The invention furthermore encompasses the use of the apparatus for sequencing a nucleic acid, and for imaging.

Any described first optical element not providing at least an off-center circular continuous intensity distribution is only intended to be applied in the embodiment relating to an apparatus comprising a first and a fourth optical element creating a second and third intensity profiles where the third intensity profile (distribution) is the convolution of two mathematical transformations corresponding to each of optical element one and four, respectively.

DETAILED DESCRIPTION OF THE INVENTION

Figure 1:
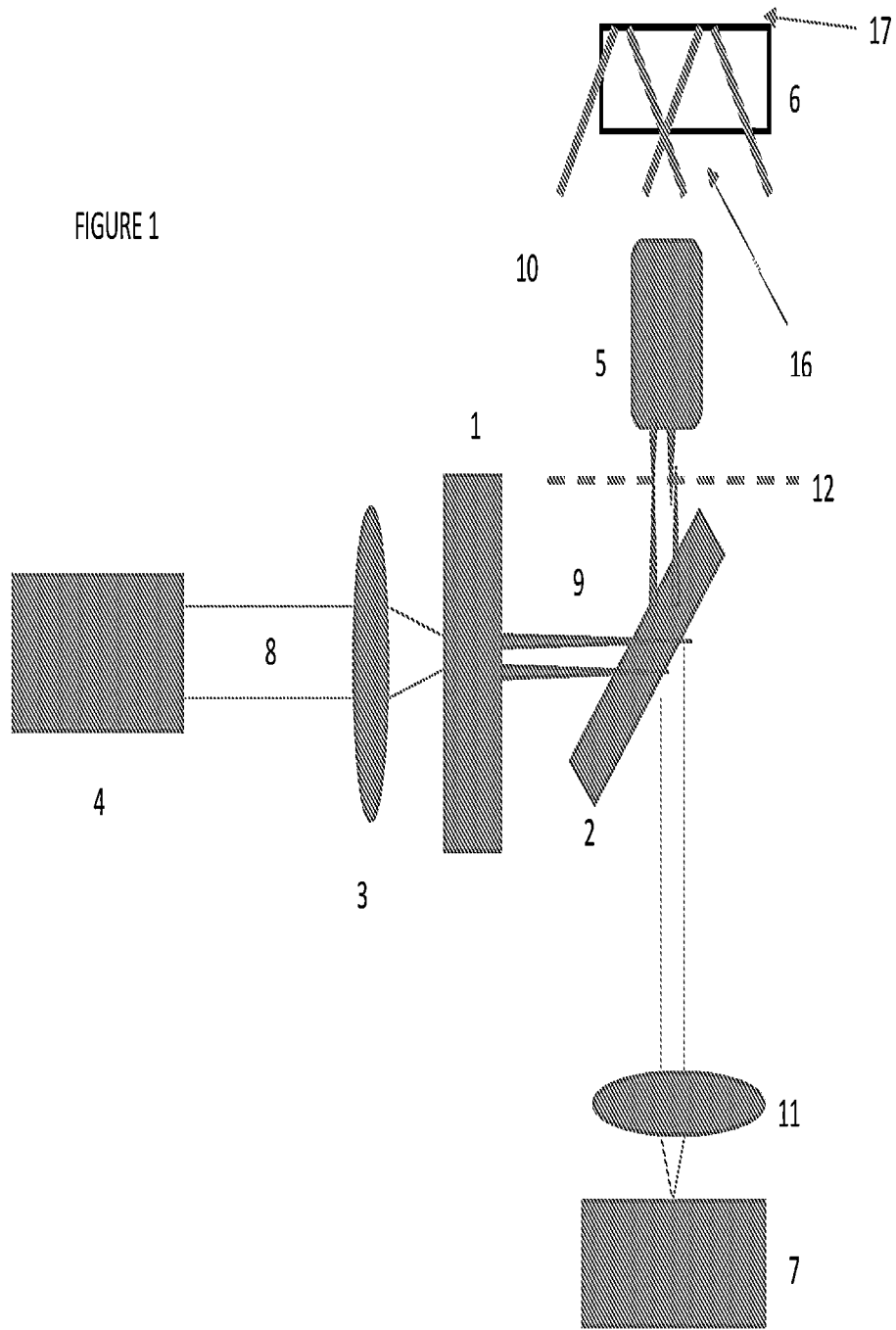
FIG. 1 shows the schematic presentation of the apparatus of the invention comprising one first optical element transforming a primary beam of radiation into a secondary intensity profile having at least an off-center circular continuous intensity profile (33).

As elaborated in the introductory part of this application an arbitrary secondary intensity profile having an off-center circular continuous intensity distribution is focused on the back focal plane of an objective. According to one embodiment relating to an apparatus having only one optical element (1) capable of transforming the intensity profile of the primary beam (8) into an arbitrary secondary intensity profile (distribution)(9), the arbitrary secondary intensity profile (9) having at least an off-center circular continuous intensity distribution (33) which is focused on the back focal plane (12) of an objective (5). Because the radiation is focused on the back focal plane of an objective, transmitted radiation of collimated shape (10) is formed at the exit of the objective. At least some of the collimated radiation will be total internally reflected on the substrate providing an evanescent field. More specifically, some of the collimated radiation has an angle with respect to the plane of phase transition at the interface substrate-solution such that the collimated radiation is total internally reflected creating an evanescent filed. The angle of the collimated radiation is dependent on the location of focusing of the arbitrary secondary discrete intensity profile on the back focal plane (x-y-plane) of the objective. Optional secondary radiation which is focused at the center of the back focal plane creates collimated radiation essentially perpendicular to the substrate. Collimated radiation perpendicular to the substrate is essentially transmitted through the substrate. Secondary radiation focused at an area of the back focal plane providing an evanescent field (or evanescent fields) is also referred to as secondary radiation (A). Any other secondary radiation not providing an evanescent filed is also referred to as secondary radiation (B). The arbitrary secondary intensity profile may also be referred to as secondary radiation relating to secondary radiation (A) and (B). The arbitrary secondary intensity profile may also be referred to as an arbitrary secondary discrete intensity distribution for the embodiment relating to an apparatus comprising at least two optical elements (i.e. a first and a fourth) capable of transforming the intensity profile of electromagnetic radiation. According to an embodiment comprising two optical elements, the arbitrary secondary intensity profile can have a beam shaped pattern. Here, the first optical element, which also may be referred to as radiation modifying optical element, transforms the incident primary radiation (beam) into at least one beam typically with a Gaussian intensity distribution.

The term discrete intensity profile does not embrace a continuum of radiation obtained e.g. by a prism. Hence, the first optical element may also be defined as being capable of transforming the intensity profile of a first primary beam into an arbitrary secondary intensity profile by means of phase-separation (of radiation) and/or modification of the polarization (of the radiation). The first optical element may also be defined as being capable of transforming the intensity profile of a first primary beam into an arbitrary secondary intensity profile by means of phase-separation (of radiation). Furthermore, the first optical element may also be described as an optical element capable of transforming the intensity profile of at least a primary radiation into an arbitrary secondary discrete intensity profile not having the characteristic of a continuum. According to an embodiment, the first optical element is capable of transforming the intensity profile of the primary beam into one (or at least one) discrete secondary beam. The first optical element may also be capable of transforming the intensity profile of the primary beam into at least two discrete secondary beams. The number of discrete secondary beams is only limited by technical limitations of the first optical element. According to yet another embodiment, the first optical element is capable of transforming the intensity profile of the primary beam into an off-center continuous circular intensity profile. It should be understood that the secondary intensity profile (optionally in the form of beams) elaborated above is (are) focused at a location(s) on the back focal plane of an objective such that collimated beam(s) exit the objective with an angle to create an evanescent field(s) at the substrate. According to one embodiment of the invention the first optical element is configured to transform the intensity profile of the primary beam into a plurality of secondary beams, at least two, all beams being focused on an area of the back focal plane of the objective creating collimated beams which all are total internally reflected on the substrate. Alternatively, the first optical element is configured to transform the intensity profile of the primary beam into a plurality of secondary beams, of which some of the secondary beams (may also be referred to as secondary beams (B)) are focused on areas of the back focal plane creating collimated beams which are not total internally reflected on the substrate. If only total internally reflected collimated beams are wanted a filter may be applied blocking any secondary beams (secondary beams (B)) producing collimated beams which are not total internally reflected on the substrate.

According to yet a further embodiment the first optical element is configured to transform the intensity profile of the primary beam into a secondary intensity profile having at least an off-center circular continuous intensity distribution. An off-center circular continuous intensity distribution is characterized as having a measurable intensity at a set radius from the optical axis of the objective. Suitably, the lowest intensity of the off-center circular continuous intensity is not lower than 50%, not lower than 20%, not lower than 10%, not lower than 5%, not lower than 1%, than the highest intensity.

The secondary beams of a circular pattern are suitably arranged at the same radii from the center (off-center circular pattern) and the same distance center-to-center of each secondary beam. The first optical element may also be configured to transform the intensity profile of the primary beam into more than one circular pattern of discrete secondary beams off-center. The first optical element may also be configured to transform the intensity profile of the primary beam into a secondary intensity profile comprising such a high a number of secondary beams (A) arranged in a circular pattern such that an almost continuous circular beam is formed. The secondary beams may have a spatial x-y-arrangement that with suitable optical elements, e.g. optical focusing elements (third optical element), can be focused on areas of the back focal plane of the objective to provide angular collimated beams which are total internally reflected on the substrate. Such secondary beams are also referred to secondary beams (A). The beam modifying optical element may be configured to transform the intensity profile of the primary beam into two discrete secondary beams (A), or multiple discrete secondary beams (A), such as 3, 4, 5, 6, 7, 8, 9, 10, 11, 12, 13, 14, 15, 16, 17, 18, 19, 20, up to a number which is governed by the limit of the resolution of the light being used. According to a further embodiment the first optical element can be configured to transform the intensity profile of the primary beam into both at least a secondary beam (A) capable of providing (ultimately) an evanescent field and at least a further secondary beam (B) (ultimately) providing a collimated beam perpendicular to the substrate. The secondary beam (A) is focused on a location of the back focal plane of the objective to give a collimated beam which is total internally reflected on the substrate creating an evanescent filed on the opposite side of the substrate. The secondary beam (B) is focused on or around the center of the back focal plane of the objective to give a collimated beam which is impinging essentially perpendicular to the substrate, being essentially transmitted through the substrate. Hence, any secondary beam (or radiation) denoted (A) is total internally reflected (TIR) providing an evanescent filed. Any secondary beam (or radiation) denoted (B) provides a collimated perpendicular to the substrate being essentially transmitted providing epi illumination. Consequently, a first optical element configured to transform the intensity profile of the primary beam into secondary beams (A) and (B) will create both TIR and EPI illumination of the substrate. This mode of illumination is specifically useful for imaging applications.

Provided that a secondary intensity profile has at least an off-center circular continuous intensity distribution or that more than one tertiary beam is focused on the back focal plane of an objective, collimated beams are formed creating overlapping evanescent fields. By overlapping several evanescent fields possible defects and diffraction patterns of individual fields are effectively suppressed since it is the convolution of all fields that forms the final evanescent field area. Also, the shape of the final evanescent field area becomes the convolution of all shapes which gives the possibility to control the shape of the area by selection of how the primary beam is split into secondary beams by the use of an optical element. By combining several evanescent fields the resulting convoluted field will be much more uniform than the individual fields. By focusing a secondary intensity profile having at least an off-center circular continuous intensity distribution on the back focal plane one receives an evanescent field with unparalleled uniformity and intensity and minimized diffraction patterns.

According to yet a further embodiment the first optical element also accommodates properties which allow focusing of the radiation, such as focusing the primary beam (3). If the first optical element incorporates focusing properties then one can dispense with the third optical element which focuses the secondary intensity profile on the back focal plane of the objective. If the first optical element also comprises focusing properties it is suitably a diffractive optical element.

The arbitrary secondary intensity profile (distribution) may be achieved by a diffractive optical element which has been modified by applying mathematical procedures.

The first optical element typically transforms the intensity profile of electromagnetic radiation to an arbitrarily secondary beam profile, or transformed beam profile. The transformed beam profile can have a continuous or discontinuous shape (in the x-y plane), such as two or more continuous shapes separated by areas without electromagnetic radiation. The transformed beam profile can have any type of intensity distribution (as long as the profile has at least one discrete sub-profile).

The first optical element can be an optical beam splitting element.

According to a further embodiment the first optical element (first and fourth and optionally further beam modifying optical elements) is a diffractive optical element, DOE.

The first optical element may also be referred to an intensity profile transforming optical element.

If two or more optical elements capable of transforming the intensity profile are incorporated the transformed beam profile represents the convolution of two of more mathematically transformations corresponding to each respective intensity profile transforming optical element. Multiple intensity profile transforming optical elements can be placed after another is any order. Focusing means are preferably positioned before or after the stack of intensity profile transforming optical element.

Diffractive optical elements may be three dimensional optical gratings applied to an optically transparent element diffracting light with the purpose of dividing an incident light beam into multiple discrete light beams. Suitable diffractive optical elements are described in the publication by Johansson and Hard, Applied Optics 38(1999), 1302-1310. DOEs can be fabricated to provide complex illumination patterns. Several approaches can be used to design and fabricate DOEs. DOEs are preferably used together with a source of light providing a relatively narrow spectral range and a coherent beam, such as light sources commonly referred to as lasers. The purpose of the DOE is to divide a beam of light with the characteristics of having a narrow spectral range and being spatially coherent into a number of discrete secondary beams. The sum of intensities of all secondary beams correspond to the intensity of the primary incident beam. The DOEs may provide patterns referred to as orders the zero order being a secondary beam which is parallel to the incident primary beam of light. The intensities of the secondary beams may vary, such that every order of secondary beams has essentially the same intensities.

DOEs typically provide beam pattern of different orders ranging from zero order up to an arbitrary order. Usually, secondary beams of zero order are focused at the center of the back focal plane of the objective providing a collimated beam exiting from the objective and being essentially perpendicular to the substrate. Collimated beams perpendicular to the substrate will essentially be transmitted through the substrate providing epi illumination on the second side of the substrate. Higher order secondary beams are typically focused on locations of the back focal plane of the objective that provide collimated beams which are not perpendicular to the substrate. It is important that at least one order of the diffraction pattern provides secondary beams which are focused on locations of the back focal plane to provide collimated beams which are total internally reflected on the substrate.

Each of the secondary beams (A) provided by the fourth optical element and focused on the back focal plane of the objective provides a collimated angular beam and creating an elliptically shaped evanescent filed in the x-y-plane on the second side of the substrate. Secondary beams (A) having same radial distance to the optical center will create elliptically shaped evanescent fields in the x-y-plane, however, angularly displaced. Hence, an increase of then number of secondary beams (A) creates an increasingly circular evanescent filed in the x-y-plane.

According to yet another embodiment, the first optical element may be an axicon lens or axicon lenses. An axicon lens has a conical surface. An axicon lens can transform a beam shaped radiation into a ring-formed radiation. Further, an axicon lens can transform a Gaussian intensity profile into a Bessel intensity profile (of a beam).

The intensity distribution of any beam, whether primary, secondary, or collimated beam, may have a variety of shapes ranging between Bessel field and Gaussian filed. Usually, the intensity distribution is best approximated with a Gaussian intensity distribution. Particularly, the collimated beams 'downstream' the objective may have a Gaussian intensity distribution.

The excitation light path, also referred to as the path of illumination of the incident beam of light, and denoting the path of light between the source of light and the substrate, may be configured as (in) a straight line, Yet, dependent on the type of optical elements this excitation light path may not be in a straight line.

The emission light path, signifying the path of the light consisting of light emitted from the luminescent entities, and ultimately captured by the detector, is separated from excitation light path typically by an optical element capable of separating (discriminating) light by wavelength, such as a dichroic.

According to one aspect of the invention the secondary beams, e.g. both secondary beams (A) and (B) or any other secondary beams, may be passed through a further optical element (fourth optical element) capable of transforming the intensity profile of radiation. Theoretically, a multitude of optical elements capable of transforming the intensity profile of radiation may be stacked after another in the direction of the excitation radiation, whereby an ever increasing complex profile is obtained, i.e. with each optical element capable of transforming the intensity profile of radiation an ever increasing number of discrete beams of radiation can be obtained. According to an embodiment, first and fourth optical elements (and any further intensity transforming optical elements) are diffractive optical elements, where the finally obtained intensity profile (distribution) is the convolution of two (or more) mathematical transformations corresponding to each of optical element one and four (or any further intensity transforming optical element), respectively A further aspect of the invention is the combined use of collimated beams of light which are totally reflected (or: total internally reflected) and collimated beams of light impinging perpendicular with respect to the substrate. For this aspect, an optical beam modifying element is used which provides a circular continuous secondary beam or at least secondary light beams (A) and further a secondary beam (B). The circular continuous secondary beam or secondary light beams (A) are focused on the back focal plane of an objective such that the transmitted photons provide collimated beam(s) of light (A) has/have an angle with respect to the substrate capable of providing an evanescent field by total internal reflection. The secondary light beams (B) are focused on the back focal plane of the objective such that the transmitted photons provide a collimated beam(s) of light perpendicular to the substrate. According to this aspect a beam splitting optical element is used providing both epi illumination and total internal reflection illumination (TIR). The aspect of the invention is specifically relevant for imaging applications.

The term secondary beams of light, termed secondary beams (A) and (B) and other secondary beams, refers to the beams of light being focused on the back focal plane of an objective, irrespective if one or several light beam modifying optical elements have been applied in the apparatus or the method. The term other secondary beams relates to secondary beams not falling under the definition secondary beams (A) and (B), such as secondary beams focused on the back focal plane of the objective producing collimated beams with an angle such that the collimated beams are not total internally reflected on the substrate nor producing collimated beams perpendicular to the substrate.

The secondary beam or beams of light must be focused on the back focal plan of the objective. If the primary beam of light is collimated an optical focusing element must be present in the path of the excitation illumination. The optical focusing element may be positioned at any location in the excitation illumination light path as long as the secondary beams of light are focused on the back focal plane of the objective. The optical focusing element may be positioned before or after the beam splitting optical element or elements.

A second optical element capable of separating (discriminating) light by wavelength is usually also present capable of separating the light emitted from the luminescent entities from the excitation light. Normally, the second optical element is a dichroic. The apparatus may also comprise a filter which is placed between the first optical element and the objective to remove undesired beams. Undesired beams may denote beams stemming from diffractive orders not being total internally reflected at the substrate. Alternatively, undesired beams may denote beams stemming from diffractive orders not being total internally reflected at the substrate but not including beams from zero order diffraction. The filter may also be an emission filer blocking excitation radiation but letting through emission photons from the luminescent entities in the solution.

According to a further embodiment the apparatus comprises an optical component (Z) which is added before the first optical element which change the size of the beam resulting in a modifiable size of the evanescent field. The optical component (Z) is preferably a beam expander comprising lenses with different focal length positioned at a distance from each other such that they change the size of the beam but not the collimation.

According to yet a further embodiment the source of electromagnetic radiation is coupled through a fiber and the optical component (Z) is a fiber out-coupler and a lens, where the lens is positioner at a distance in relation to its focal length and the fiber out-coupler.

Figure 6:
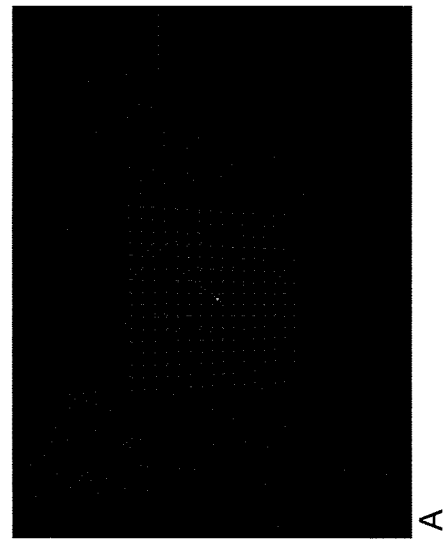
Figure 6:
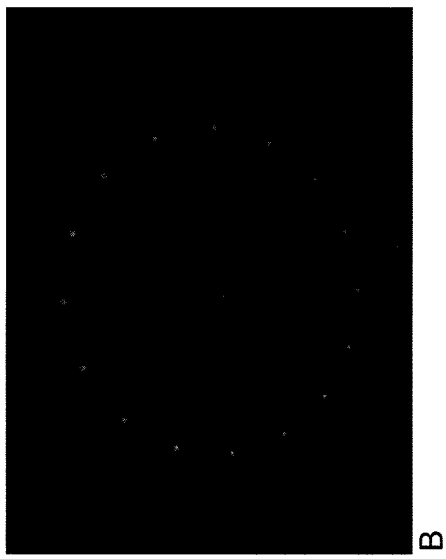
Figure 6:
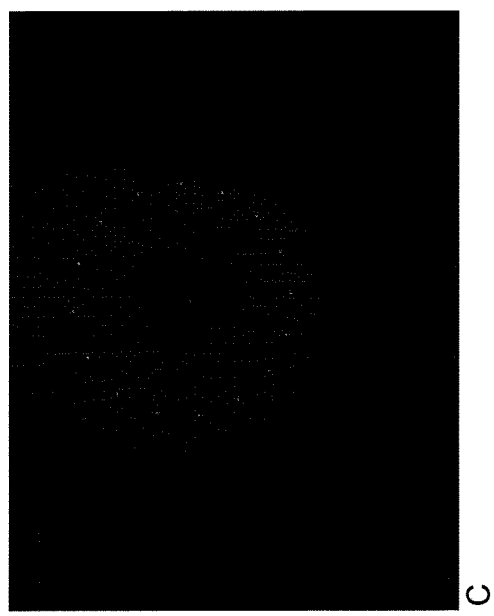

A yet further aspect of the invention relates to an apparatus combining an evanescent filed and confocal illumination of the solution comprising luminescent entities. FIG. 6 shows a schematic configuration of an apparatus providing both total internal reflection (TIR) illumination and confocal illumination. 4 and 4a denotes lasers. The optical pathway (indicated by full lines) of laser 4 corresponds to the set-up of FIG. 1 where a DOE splits the beam (8) into several discrete secondary beams (9) which are focused on the pack focal plane of the objective (5). The secondary beams exit the objective as collimated beams impinging on the substrate (6) at an angle creating an evanescent field. The collimated beam of laser 4a is split into multiple beams by a DOE (1a). Unlike the secondary beams originating from the radiation of laser 4, the multiple beams from laser 4a are not focused on the back focal plane of the objective (5). Instead, said beams enter the back focal plane of the objective (5) as non-focused collimated beams. The collimated beams entering the objective will be focused within the solution comprising luminescent entities providing multiple confocal volume elements within the solution. By suitable wavelength discrimination means, such as dichroics, the emission radiation is separated from the excitation radiation and guided to a detector (7). The detector (7) may be arranged in a z direction inform or behind the figure x-y-plane.

Source of Light

The electromagnetic radiation provided by the source is suitably light. The electromagnetic radiation has typically a wavelength in the range of form about 100 nm up to about 2000 nm. Preferred radiation has a wavelength in the range of from about 300 nm up to about 900 nm, suitably form about 350 nm up to about 850 nm. Preferably, the electromagnetic radiation is in the visible spectrum. According to a preferred embodiment the electromagnetic radiation is coherent with a narrow wavelength distribution. Preferably, the electromagnetic radiation is provided by a laser providing a primary beam of coherent, collimated light with a very narrow wavelength distribution. Specifically preferred light sources include any types of lasers e.g. solid state laser diodes. The apparatus may comprise more than one excitation light sources. If more than one light source is applied, the sources of light suitably have non-overlapping wavelengths.

Substrate

The substrate may be produced of a variety of materials and may have a variety of shapes. Suitable, the substrate comprises a material which is capable of providing an evanescent filed under the circumstances elaborated in this document. Preferably, the substrate also has the properties of transmitting light which impinges perpendicularly to the surface of the substrate. The configuration of the substrate is dependent on the type of application. According to an embodiment the substrate has a plurality of discrete areas which are configured for the immobilization of biomolecule complexes (which are elaborated in more detail further down) and which are aligned with discrete areas of the detector. Such discrete areas of the detector may be one or several pixels of a multipixel-type detector. By suitable optical components in the emission light pathway, i.e. the path of the emitted light from the luminescent entities to the detector, the luminescent events occurring at a volume correlated to discrete areas configured for the immobilization of luminescent entities can be properly aligned with detection pixels of a multipixel type detector. Usually, the discrete areas of the substrate configured to immobilize the luminescent entities can be made smaller than the sub-units of the multipixel detector. Hence, suitable optical magnifying components may be present in the path of the emitted light. The areas of the substrate configured for immobilization of the luminescent entities may range from $5*10-19$ up to $10-14$ m2. If the areas would be circular the values signify diameters of from about 1 nm up to 100 nm. The minimal distance between areas of circular proportions for immobilization is governed by the production technique and quality of the mutipixel detector specifically in terms of cross-talk of adjacent sub-units of the detector. Preferably, the minimal distance center-to-center between areas of circular proportions for immobilization should exceed 20 times the diameter. Preferred configuration of the substrate in combination with a detector is disclosed in published patent application WO 2015/104245, which is incorporated by reference. Many of the phenomena occur in aqueous solutions. Hence, the substrate may have design features accommodating aqueous solutions.

Detector

The detector is preferably a semiconductor detector, e.g. a solid state detector. Semiconductor detectors for counting photons may have a surface absorbing photons and producing an entity proportional to the absorbed photons, e.g. current, voltage. The detector may be a semiconductor based on a p-n-junction reversed-biased at a voltage Va exceeding the breakdown voltage of the junction. Single-photon avalanche diodes (SPAD) are based on the concept just mentioned.

Preferably, the detector is a semiconductor detector based on the concept of SPAD, comprising a multitude of discrete sub-detection units. The discrete sub-detection units may be regarded as pixels or an array of pixels. In the application of sequencing nucleic acid, each discrete sub-detection unit is carefully aligned with the areas of the substrate configured for immobilization of at least one biomolecular complex. Preferably, the semiconductor detector has a single photon sensitivity, specifically in the visible and near infrared wavelength range. Preferably, the detector is based on SPADs integrated in electric circuitry based on CMOS technology. With the CMOS technology in principle, the amount of discrete sub-detection units may be correlated to a single pixel element of a CMOS detector. Hence, the resolution of the sub-detection units of a SPAD-CMOS detector is in principle correlated to the continuous increase in the number of pixels of a CMOS sensor. Today, a 50 mega pixel CMOS sensor is commercially available.

While the instrument may comprise a pinhole filter in the emission path the sub-detection units of the detector may also serve as pinholes. As already elaborated above, the detection volume on the second side of the substrate may be defined by the evanescent field and the area of the pinhole, or, the area of the sub-detection units of the detector.

Hence, the detector may be a SPAD detector comprising up to e.g. 10 mega sub-detection units said sub-unit detection areas comprising pixels (or several pixels, e.g. from 2 to 50 pixels). By suitable optical means said sub-detection units are each aligned with discrete area of the substrate of a number corresponding to the number of sub-detection units of the detector, said discrete area comprising at least one biomolecule complex where free luminescent entities, such as fluorescent labelled nucleotides, are incorporated.

The emitted light may be detected with a light detector which comprises a plurality of detection pixels aligned with the discrete areas of support configured for the immobilization of at least one biomolecule complex. Preferably, the detector is a multipoint single photon avalanche detector (SPAD). It combines high sensitivity over a broad spectral range, e.g. 350-900 nm with a high time resolution of e.g. <1 ns, which is advantageous when the lifetime of an excited fluorescent state is to be used for molecular analysis.

FIG. 1 depicts an embodiment of the apparatus of the invention. A first beam of coherent laser light (8) is provided by a laser source (4). The first beam is focused by a lens (third optical element) and split up into a secondary intensity profile having at least an off-center circular continuous intensity distribution (9) by the DOE (1) (first optical element). The secondary intensity profile having at least an off-center circular continuous intensity distribution is focused on an area of the back focal plane of the objective (5). Collimated beams (10) exit the objective (5) at an angle α being total internally reflected at the substrate (6). The substrate has discrete areas comprising at least one biomolecule complex and an aqueous solution with at least free nucleotides linked to a fluorescent compound. The evanescent filed provided by total internal reflection (TIR) of the collimated light excites the fluorescent compounds. The emitted photons are separated from the excitation light by a dichroic (2) focused (11) and captured by a detector (7). The emitted photons are used for evaluation/characterization/analyzation of static as well as temporal phenomena occurring within the evanescent field by e.g. application of any one of the following concepts: (i) the excited state lifetime of the emitted photons; (ii) the number of emitted photons per unit of time; (iii) the residence time of the luminescent entities while associated to the biomolecule complex; (iv) the energy of the emitted photons; (v) the polarization of the emitted photons; (vi) the wavelength of the emitted photons. The sequences of nucleotides may be evaluated by only relying of one of the mentioned concepts or any combination of concepts be it a combination of two, three, four, five or all six concepts. In FIG. 1 (x) denotes the back-focal plane of the objective, (y) denotes the object plane, and (z) denotes the image plane.

Figure 2:
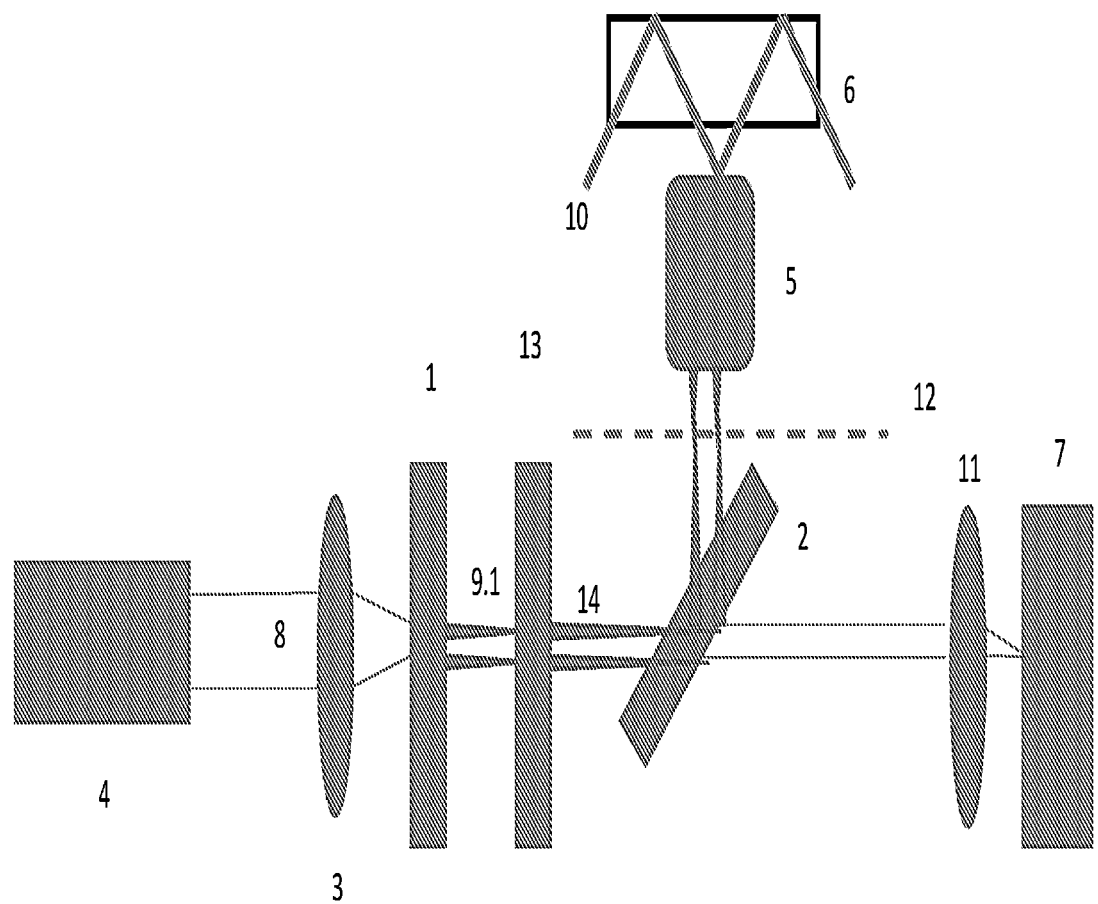
FIG. 2 shows a schematic presentation of an apparatus comprising two optical elements (1) and (13).
Figure 5:
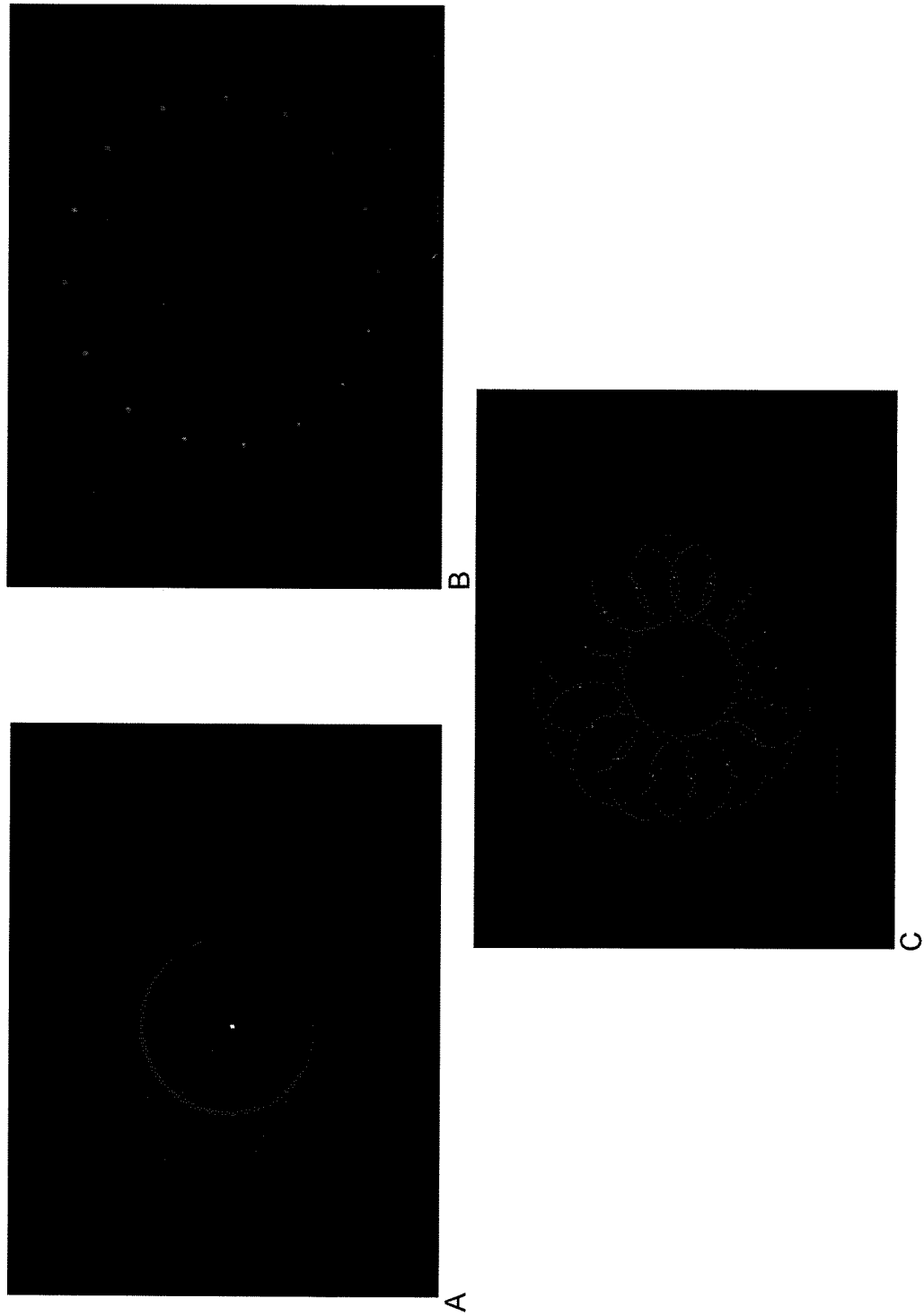
FIGS. 5 and 6 show the intensity profiles (A)(B) of a first and forth optical element and the convolution (C) of said intensity profiles (A) and (B) (also referred to as third intensity profile).

FIG. 2 shows an apparatus comprising two optical elements. The first fourth optical element (1, 13) transform a first intensity profile into a secondary intensity profiles (9.1: FIGS. 5 and 6 pictures A and B). The third intensity profile (14) is the convolution of the two mathematical transformations corresponding to each of first and fourth optical elements (1, 13: FIGS. 5 and 6 pictures C).

Figure 3:
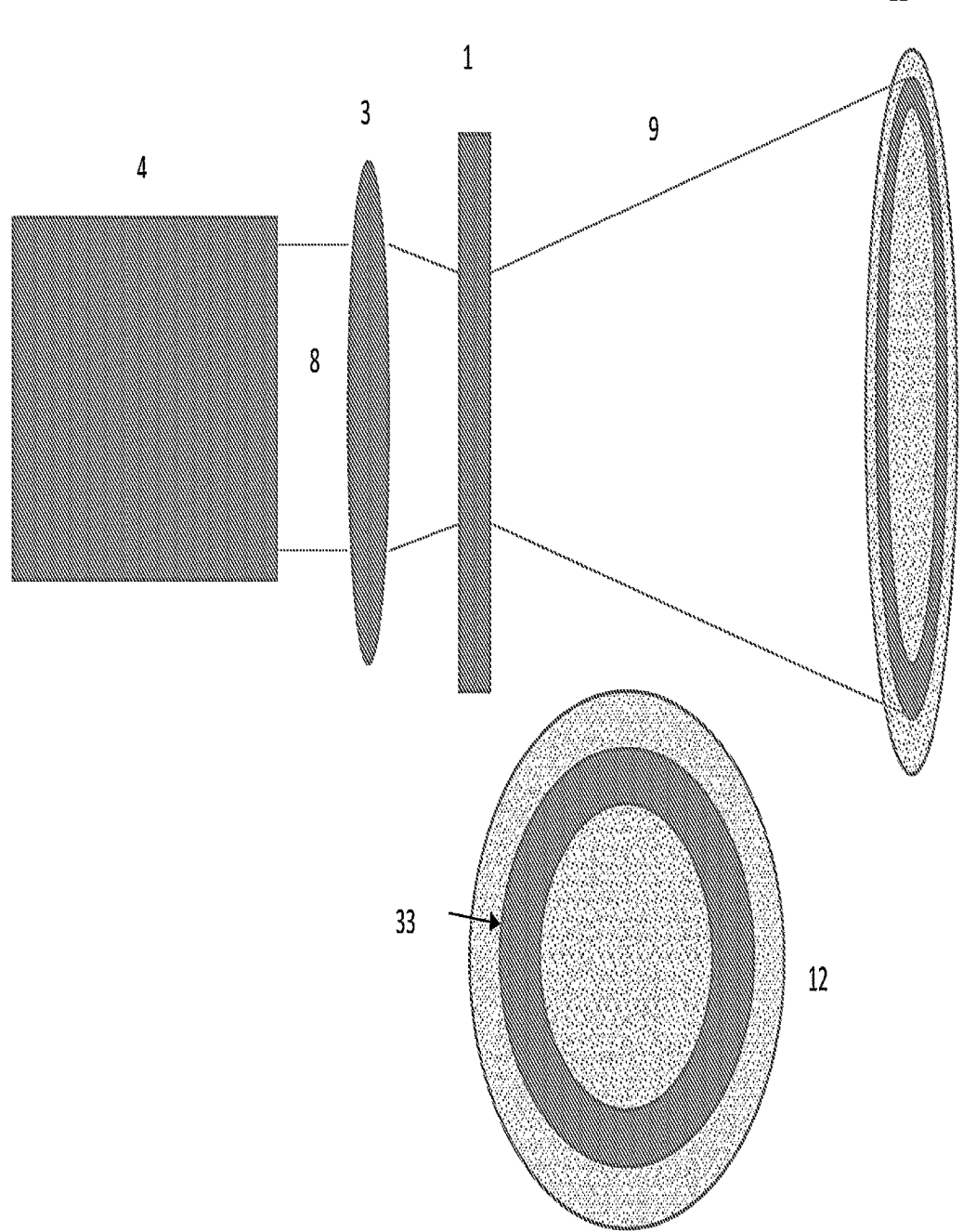
FIG. 3 depicts schematically a secondary intensity distribution having an off-center circular continuous intensity distribution.

FIG. 3 show part of the apparatus and inter alia a first optical element (1) transforming the intensity profile of the primary beam (8) into a secondary intensity profile (9) having at least an off-center circular continuous intensity distribution (33) which off-center circular continuous intensity distribution is focused on the back focal plane (12). FIG. 3 shows a primary beam (8), a focusing lens (third optical element, 3), a first optical element (1), secondary intensity profile (9) and the focusing on the back focal plane (12) of an objective.

Figure 4:
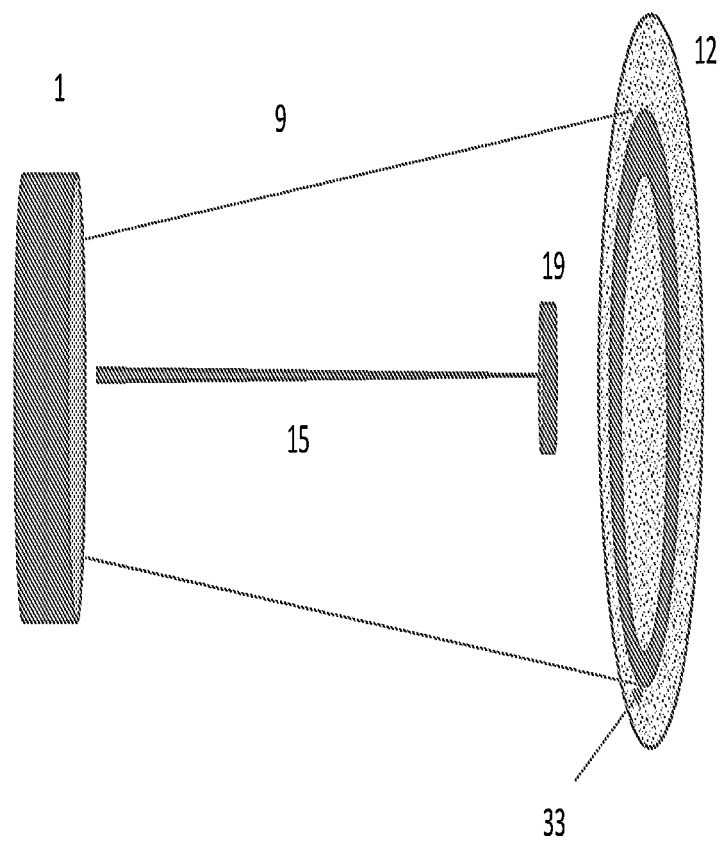
FIG. 4 shows an exemplified configuration of the apparatus comprising a filter which blocks undesired secondary beams.

FIG. 4 shows an embodiment comprising a first optical element (1), a filter (112) blocking undesired radiation, e.g. any radiation not providing evanescent fields, and the back-focal plane (12). The optical element (1) transforms an impinging beam into a secondary intensity profile (9) having at least an off-center circular continuous intensity distribution (33) focused on the pack-focal plane (12) to give evanescent filed at the substrate, while a further secondary beam (19) (of zero order) is blocked with the filter (19). The zero order beam would, if not blocked, be transmitted through the substrate.

FIGS. 5 and 6 show the intensity profiles (A)(B) of a first and forth optical element and the convolution (C) of said intensity profiles (A) and (B) (also referred to as third intensity profile)

Figure 7:
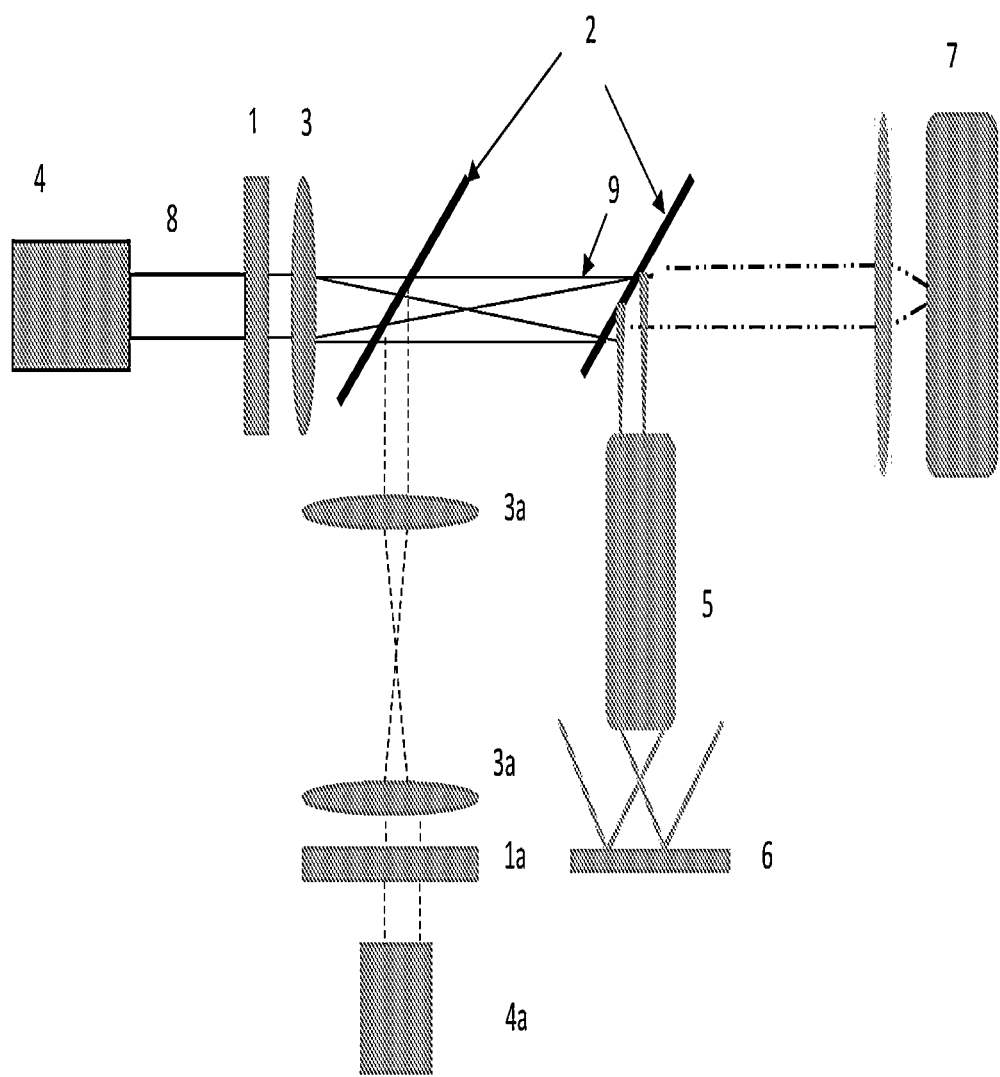
FIG. 7 shows an apparatus combining an evanescent filed and confocal illumination.

FIG. 7 shows an apparatus combining an evanescent filed and confocal illumination.

Figure 8:
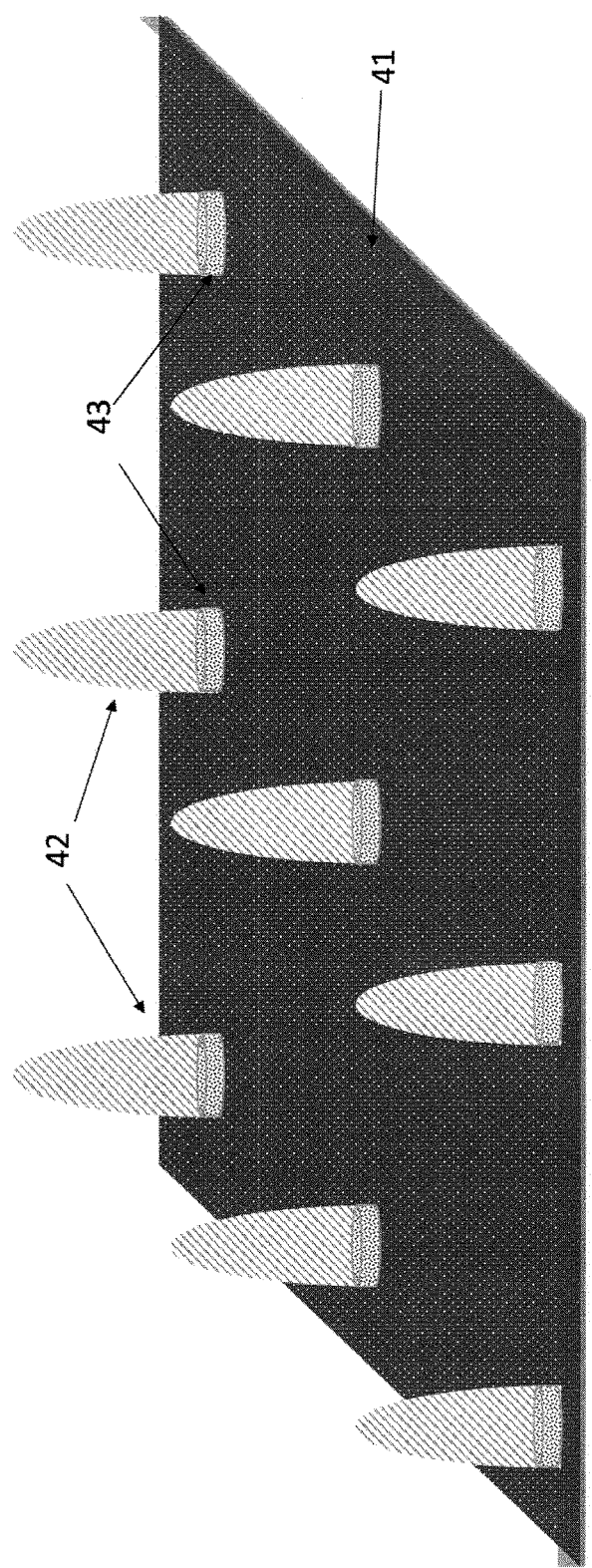
FIG. 8 shows part of the evanescent field (41) on one side of the substrate and the volume provided by the pinhole of the sub-unit of the detector (42). Volumes (43) denote an evanescent field confined by the sub-unit of the detector (43). The biomolecular complex is suitably immobilized on the substrate which coincides with volume (43)

FIG. 8 depicts part of the evanescent field (41) on one side of the substrate and the volume provided by the pinhole of the sub-unit of the detector (42). Volumes (43) denote an evanescent field confined by the sub-unit of the detector (43). The biomolecular complex is suitably immobilized on the substrate which coincides with volume (43).

Also, by overlapping several evanescent fields possible defects and diffraction patterns of individual fields are effectively suppressed since it is the convolution of all fields that forms the final evanescent field.

Applications

The present instrument and method is preferably applied for characterization of biomolecules, such as nucleic acids, proteins, or other molecules occurring in living organisms, in particular in mammals such as humans. It is also possible to characterize analytes which have been produced from biological samples in vitro, such as cDNA produced from mRNA by reverse transcription, or proteins which have been produced by mRNA or DNA by vitro translations. The invention is also suitable for the detection of analytes which are present as elements of a library and are intended to exhibit predetermined characteristics, such as binding to the detector reagent. Examples of such libraries are phage libraries or ribosomal libraries. A particularly preferred application relates to the characterization the nucleic acids, and particularly the sequence of the nucleotides of nucleic acids. This application includes the use of an enzyme capable of incorporating a labelled nucleotide complementary to a target strand of a nucleic acid. The enzyme is suitable comprised in a biomolecule complex. The biomolecule complex typically comprises an enzyme capable of incorporating labelled nucleotides complementary to a target nucleic acid strand, a nucleic acid strand and a primer. Different entities may also be associated with the biomolecule complex. The compounds/entities of the biomolecule complex are associated to each other covalently and/or any other forces such as hydrogen bonding and/or wan der Waals forces. The luminescent entities are preferably linked to free nucleotides which when associated to the biomolecule complex with be incorporated into a growing nucleic acid strand complementary to the target nucleic acid strand. Alternatively, the luminescent entities are associated to the biomolecule at a location providing detectable signals by the detector from which the sequence of the nucleotides of the target nucleic acid strand can be derived. The luminescent entity may be linked to different parts of the nucleotide such as to the nitrogenous base, sugar, or a phosphate group. Suitably, the luminescent entity is bound to a phosphate group, and preferably to the terminal phosphate group. Preferably, the luminescent entity is a fluorescent entity, or fluorescent molecule, suitably linked to the terminal phosphate group of the nucleotide. For clarification, nucleotide refers to a molecule comprising at least a nucleo base and a sugar. The nucleotide may also denote a molecule comprising a nucelo base, a sugar, an at least a phosphate group. The nucleotide may also comprise multiple phosphate groups such as 3 or 5 phosphate groups. Commonly, the term nucleoside relates to a

The invention claimed is:

1. An apparatus for characterizing luminescent entities by excitation comprising:
    a substrate (6) being in contact with a solution comprising luminescent entities;
    a source of electromagnetic radiation providing at least a primary beam of radiation (4);
    an objective (5); a first optical element (1) capable of transforming the intensity profile of the primary beam (8) into an arbitrary secondary intensity profile (distribution) (9) by phase-separation and/or modification of polarization;
    a second optical element (2) capable of separating or discriminating radiation by wavelength; and a detector (7), wherein the detector (7) comprises a plurality of discrete sub-detection units, each discrete sub-detection unit serving as a pinhole, wherein said pinhole has an area, and wherein a detection volume on the substrate is defined by an evanescent field and the area of each pinhole, where the arbitrary secondary intensity profile has at least an off-center circular continuous intensity distribution (33) focused on the back focal plane (12) of the objective forming a collimated beam (10) capable of creating an evanescent field on the side of the substrate where the solution comprising luminescent entities are located, where the evanescent field excites the luminescent entities thereby creating emission radiation separated by the first optical element and captioned by the detector.

2. The apparatus according to claim 1, wherein the first optical element (1) is capable of transforming the intensity profile of the primary beam (9) into an arbitrary secondary intensity profile (9) by phase-separation.

3. The apparatus according to claim 1, wherein the first optical element (1) is a diffractive optical element.

4. The apparatus according to claim 1 comprising a third optical element (3) capable of focusing a light beam.

5. The apparatus according to claim 1, wherein the electromagnetic radiation is light.

6. The apparatus according to claim 5, wherein the light has a wavelength in the range of from about 300 nm to about 900 nm.

7. The apparatus according to claim 5, wherein the light is in the visible spectrum.

8. The apparatus according to claim 5, wherein the light is coherent with a narrow wavelength distribution.

9. The apparatus according to claim 5, wherein the light is laser light.

10. The apparatus according to claim 1, wherein the first optical element (1) transforms the intensity distribution of the primary beam into an intensity distribution providing at least a further secondary beam (15) focused in the center of the back focal plane (12) of the objective (5).

11. The apparatus according to claim 1, wherein substrate (6) comprises a first (16) and second (17) side, the solution comprising the luminescent entities being in contact with the second side (17).

12. The apparatus according to claim 11, wherein measurement volumes on the second side of the substrate are defined by the evanescent field and the confinement defined by the area of the discrete detections areas of the semiconductor detector.

13. The apparatus according to claim 1, wherein the diffractive index of the substrate is higher than the diffractive index of the solution comprising luminescent entities.

14. The apparatus according to claim 1, wherein the luminescent entities are immobilized on the substrate.

15. The apparatus according to claim 1, wherein the luminescent entities associate to complexes immobilized on the substrate.

16. The apparatus according to claim 15, wherein the complexes comprises a nucleic acid residue and a protein associated to the nucleic acid residue.

17. The apparatus according to claim 1, wherein the luminescent entities are luminescent molecules.

18. The apparatus according to claim 1, wherein luminescent entities are nucleotide residues comprising a fluorescent moiety.

19. The apparatus according to claim 1, wherein the second optical element is a dichroic optical element.

20. The apparatus according to claim 1, wherein the detector is a semiconductor comprising a multitude of discrete detection areas.

21. The apparatus according to claim 1, used for characterizing the sequence of a nucleic acid continuous and radial to the optical axis of the objective, the secondary continuous and radial intensity profile.

22. An apparatus for characterizing luminescent entities by excitation comprising:

a substrate (6) being in contact with a solution comprising luminescent entities;

a source of electromagnetic radiation (4) providing at least a primary beam of radiation (8);

an objective (5);

a first optical element (1) capable of transforming the intensity profile of the primary beam into an arbitrary secondary intensity profile or distribution (9);

a second optical element (2) capable of separating or discriminating radiation by wavelength;

a fourth optical element (13) capable of transforming the secondary discrete intensity profile or distribution (9.1) into an arbitrary third intensity profile or distribution (14); and a detector (7), wherein the detector (7) comprises a plurality of discrete sub-detection units, each discrete sub-detection unit serving as a pinhole, wherein said pinhole has an area, and wherein a detection volume on the substrate is defined by an evanescent field and the area of each pinhole, where first (1) and forth (13) optical elements are diffractive optical elements, where the arbitrary third intensity profile (14) is focused on the back focal plane (12) of the objective (5) such that at least a collimated beam (10) is obtained capable of creating an evanescent field on the side of the substrate where the solution comprising luminescent entities are located, where the evanescent field excites the luminescent entities thereby creating emission radiation separated by the first optical element and captioned by the detector, and wherein and the third intensity profile or distribution is the convolution of two mathematical transformations corresponding to each of optical element one and four, respectively.

23. The apparatus according to claim 22, wherein the first optical element (1) is capable of transforming the intensity profile of the primary beam into at least one discrete secondary beam (9.1).

24. The apparatus according to claim 22, wherein the first optical element (1) is capable of transforming the intensity profile of the primary beam into at least two discrete secondary beams (9.1).

\* \* \* \* \*